United States Patent [19]
Sackmann et al.

[11] Patent Number: 6,156,848
[45] Date of Patent: Dec. 5, 2000

[54] PRE-FORMED SUPER ABSORBERS WITH HIGH SWELLING CAPACITY

[75] Inventors: Günter Sackmann, Leverkusen; Sergej Schapowalow, Köln; Siegfried Korte, Odenthal; Rolf-Volker Meyer, Leverkusen, all of Germany

[73] Assignee: Bayer AG, Leverkusen, Germany

[21] Appl. No.: 08/964,069

[22] Filed: Nov. 4, 1997

[30] Foreign Application Priority Data

Nov. 13, 1996 [DE] Germany ............................ 196 46 856

[51] Int. Cl.[7] ............................ C08F 20/44; C08F 120/44
[52] U.S. Cl. ...................... 525/329.1; 524/555; 524/379; 525/329.2; 525/329.3; 525/369
[58] Field of Search ..................... 524/555, 556, 524/379; 525/329.1, 329.2, 329.3, 369

[56] References Cited

U.S. PATENT DOCUMENTS

| | | | |
|---|---|---|---|
| 3,200,102 | 8/1965 | Kleiner | 260/88.7 |
| 3,926,930 | 12/1975 | Ohfuka et al. | 260/85.5 S |
| 4,107,121 | 8/1978 | Stoy | 264/182 X |
| 4,558,100 | 12/1985 | Kightlinger et al. | 525/329.1 |
| 5,218,039 | 6/1993 | Stoy et al. | 524/566 |
| 5,252,692 | 10/1993 | Lovy et al. | 526/342 |
| 5,496,890 | 3/1996 | Sackmann et al. | 525/329.1 |
| 5,523,367 | 6/1996 | Ahmed | 526/240 |
| 5,635,569 | 6/1997 | Sackmann et al. | 525/367 |
| 5,691,421 | 11/1997 | Tanaka et al. | 525/329.2 |

FOREIGN PATENT DOCUMENTS

| | | |
|---|---|---|
| 241 885 | 4/1987 | European Pat. Off. . |
| 670 335 | 2/1995 | European Pat. Off. . |
| 697 416 | 8/1995 | European Pat. Off. . |
| 29 03 267 | 8/1980 | Germany . |
| 0 670 335 A1 | 2/1995 | Germany . |
| 44 29 318 A1 | 2/1996 | Germany . |

*Primary Examiner*—Judy M. Reddick
*Attorney, Agent, or Firm*—Connolly Bove Lodge & Hutz LLP

[57] ABSTRACT

Super-absorbent polymer in the form of pre-formed spherical particles obtainable by alkaline hydrolysis of aqueous emulsions of crosslinked and/or un-crosslinked homopolymers and/or copolymers of acrylonitrile in water/alcohol mixtures and the use of the polymer in hygiene products, as a water-storing material in agriculture and for the sheathing of electrical cables.

4 Claims, 1 Drawing Sheet

Enlargement: 250 times 0.1 mm

PRE-FORMED SUPER ABSORBERS WITH HIGH SWELLING CAPACITY

The invention relates to the production of pre-formed, spherical, super-absorbent polymers with excellent swelling capacity.

Super-absorbent polymers are known and are mainly used in the production of diapers and incontinence articles but also as water-storing materials in agriculture and in the sheathing of electrical cables. These super-absorbent polymers are generally loosely crosslinked, water-insoluble polymers or copolymers based on alkali metal salts of polyacrylic acid or copolymers of alkali metal salts of acrylic acid and acrylamide which are obtained by radically initiated copolymerisation of acrylic acid and polyfunctional monomers such as divinylbenzene, ethylene glycol dimethacrylate, ethylene glycol diallyl ether, butanediol acrylate, hexanediol methacrylate, polyethylene glycol diacrylate, trimethylolpropane diacrylate, allyl acrylate, diallyl acrylamide, triallylamine, diallyl ether, methylenebisacrylamide and N-methylolacrylamide. Owing to their structure, such polymers are capable of absorbing large quantities of water and aqueous solutions with swelling and the formation of hydrogels, and of holding these under pressure.

In the U.S. Pat. Nos. 5,496,890 and 5,635,569 as well as in European patent application (publication no. 0 670 335) and German Offenlegungsschrift 44 29 318, powdered polymers with super-absorbent properties are described which are obtained by the alkaline hydrolysis of aqueous, fine-particle emulsions of un-crosslinked and/or crosslinked homopolymers and/or copolymers of acrylonitrile. In this process the products with super-absorbent properties may be isolated as fine-particle powders by precipitating with solvents such as e.g. aliphatic monohydric alcohols. After filtering and drying, these must be brought into the desired particle size range for the application by grinding and sieving, which means a special step with considerable costs in terms of time and energy.

It is an aim of the invention to produce polymers with super-absorbent properties directly, i.e. without grinding and sieving, with the desired particle size and particle size distribution.

The invention thus relates to super-absorbent polymers in the form of pre-formed, spherical particles the particle size distribution of which is in the range of 100 to 850 $\mu$m, the proportion by mass of particles with a diameter of <100 $\mu$m being less than 10 to 15 wt. %.

The invention further relates to a process for the production of super-absorbent polymers in this particle form, wherein fine-particle, aqueous emulsions of crosslinked and/or un-crosslinked homopolymers and/or copolymers of acrylonitrile are partially hydrolysed by reaction with alkali metal hydroxides in water/alcohol mixtures and the powders precipitated during the course of the reaction are separated off, dried and optionally heated briefly.

Figure 1:
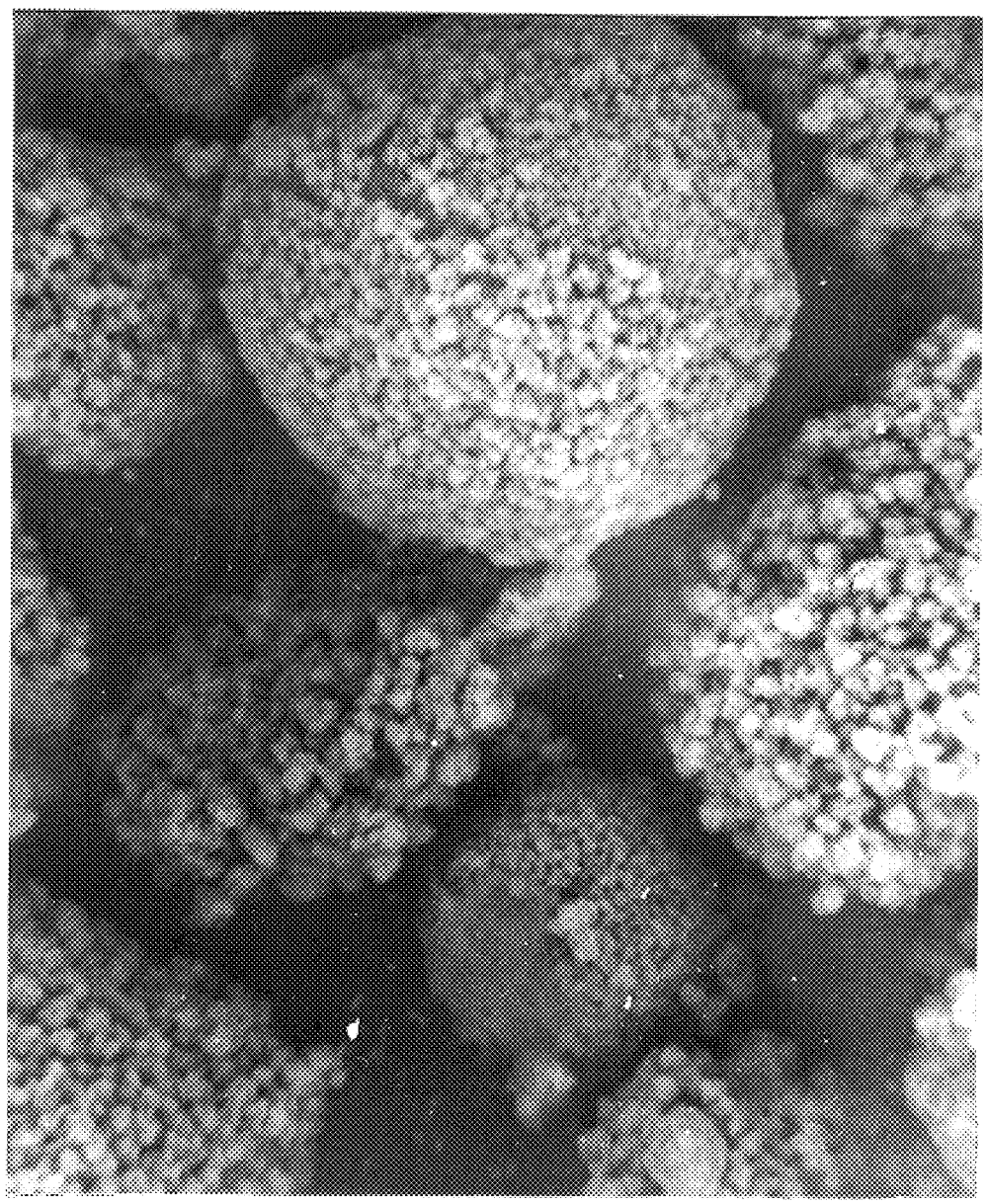
FIG. 1 is an electron micrograph showing the polymers of the present invention.

Fine-particle, aqueous emulsions of acrylonitrile homopolymers and/or copolymers (PAN emulsions), the production of which is described e.g. in European patent application—publication no. 0 590 460, are used as starting products for the production of the super-absorbent polymers according to the invention. These emulsions may contain both linear, un-crosslinked homopolymers and/or copolymers with molecular weights of $5 \cdot 10^5$ to $1 \cdot 10^7$ g/mol, preferably of $2 \cdot 10^6$ to $5 \cdot 10^6$ g/mol, and crosslinked homopolymers and/or copolymers. To produce these emulsions with solids contents of up to 55 wt. %, special anionic polymeric emulsifiers may be used which are also described in European patent application—publication no. 0 590 460.

The average particle diameters of the un-crosslinked and also of the crosslinked emulsions, determined by laser correlation spectroscopy, are in the range of 100 to 200 nm. In order to obtain emulsions which contain crosslinked homopolymers and/or copolymers of acrylonitrile, polyfunctional monomers such as e.g. divinylbenzene, ethylene glycol dimethacrylate, triallylamine etc. are used in the polymerisation in quantities of 0.2 to 4.0 wt. %, based on acrylonitrile.

The pre-formed, spherical polymers with super-absorbent properties are obtained by reacting the fine-particle polymer emulsions with alkali metal hydroxides in water/alcohol mixtures at 50 to 100° C. The molar ratio of the nitrile groups of the starting polymers to the hydroxyl groups of the alkali metal hydroxides is preferably 1:1 to 1:0.1, particularly preferably 1:0.8 to 1:0.5.

Primary, aliphatic, monohydric alcohols such as e.g. methanol, ethanol, n-propanol, i-propanol, n-butanol or i-butanol are used as the alcohols. The weight ratio of water to alcohol is 10:1 to 1:10, preferably 5:1 to 1:5, more preferably 2:1 to 1:2. Both the average particle diameter and the particle size distribution may be controlled through the water:alcohol ratio and the type of alcohol. Thus, with an increasing proportion of alcohol, products with a smaller average particle diameter and a narrower particle size distribution are obtained. The water solubility of the alcohol also influences the average particle diameter and the particle size distribution. Thus, alcohols with very good water solubility, such as methanol or ethanol, lead to products with a lower average particle size while hydrolysis in the presence of n-propanol or i-propanol gives products with a larger average particle diameter.

The average particle diameters in the range of 100 to 850 $\mu$m required for the use of these polymers in the hygiene sector may be obtained according to the invention without grinding and sieving. The process may be conducted in such a way that the proportion of polymer particles with a particle diameter of <100 $\mu$m is between 5 and 15 wt. %.

During hydrolysis the fine-particle emulsions based on polyacrylonitrile are converted into a readily stirrable suspension which can be filtered and dried without difficulty on completion of the reaction. FIG. 1 shows an electron micrograph of the super-absorbent polymers obtained by the described method. Discrete particles with spherical morphology and a strongly structured surface are clearly visible.

The products obtained in accordance with the claimed process exhibit excellent super-absorbent properties: for example their free swelling capacity in water and in 0.9% NaCl solution is up to 700 g/g and up to 60 g/g respectively and the centrifuge capacity (C.C.) is up to 45 g/g.

Another advantage of these products is that they exhibit high gel strength in the swollen state and the swollen, spherical particles promote the further transport of additional liquid released. This property is particularly desirable for the production of hygiene articles such as e.g. babies' diapers, since so-called "gel blocking" is prevented by the use of such products.

By subsequently heating the super-absorbent polymers obtained to 150 to 250° C., preferably 170 to 210° C., for 2 to 30 minutes, preferably 5 to 15 minutes, their already excellent applicational properties can be improved still further. This relates particularly to the swelling kinetics, i.e. the rate of absorption for water and other liquids, and the gel strength of the swollen polymers and their absorption capacity for aqueous liquids under pressure.

The super-absorbent polymers are highly suitably for use in the production of hygiene articles, such as e.g. babies' diapers or incontinence products, and for the sheathing of electrical cables. In addition, the products may be used in agriculture as water-storing materials.

EXAMPLES

Example 1

358.8 g of a fine-particle (average particle diameter: 95 nm), aqueous polymer emulsion composed of 99.25 wt. % acrylonitrile and 0.75 wt. % divinylbenzene, having a solids content of 22.16%, and 100 g of ethanol are placed, with stirring, in a 2-liter, four-necked flask equipped with a reflux cooler, thermometer, dropping funnel and stirrer. The contents of the reactor are heated to 50° C. A mixture of 115 g of ethanol and 90.4 g of a 45.0 wt. % aqueous NaOH solution is then added. This gives an initial reaction mixture with the following composition: 12.0 wt. % polyacrylonitrile and 6.14 wt. % NaOH, the molar ratio of polyacrylonitrile to NaOH being 1:0.68 and the weight ratio of water to ethanol being 1:0.65.

The reaction mixture is heated to 78 to 79° C., with stirring and with $N_2$ being passed over. When a degree of hydrolysis of 58.5% has been reached—established by quantitative determination of the ammonia split off—it is cooled to 20° C. After cooling, a mixture of 450 g of ethanol and 53.5 ml of a 5-molar formic acid solution is metered into the reactor for 15 minutes to neutralise the unreacted sodium hydroxide solution. After filtering and washing with 500 ml of ethanol and drying in vacuo at 65° C., 127 g of a colourless powder is obtained which is graded by sieving without grinding.

Particle size distribution: <100 μm: 12.5 wt. %; 100–850 μm: 87.5 wt. %.

Thermal Treatment

The polymer obtained according to Example 1 (average particle diameter: 100–850 μm) is kept at a temperature of 165° C. for approx. 15 minutes in a forced-air drying cupboard.

Determination of the Degree of Swelling 250 mg of the super-absorbent polymer to be investigated are weighed into a 300-ml beaker, 250 to 300 ml of distilled water or 50 ml of a 0.9 wt. % NaCl solution are poured over and the polymer is left to stand. When the equilibrium state of swelling is reached, the gel obtained is filtered through a filter cloth with a 30 μm mesh size or a paper filter and weighed. The degree of swelling is then calculated from the ratio of end weight:initial weight in g/g. Each determination is carried out three times. The measuring accuracy is ±5%.

For the product prepared in accordance with Example 1 the degree of swelling after thermal treatment is 505 g/g in distilled water and 56.8 g/g in 0.9% NaCl solution.

Determination of pH

The pH value of the product obtained in accordance with Example 1 in 0.9% NaCl solution is 5.7.

Determination of the Water-Soluble Portion (WSP)

0.5 g of the super-absorbent polymer is placed into 500 ml of de-ionised water and stirred for 16 hours at 20° C. After filtering the gel, the WSP is obtained from the determination of the solids content in the filtrate and washing water. In the case of the product obtained in accordance with Example 1 this is 7.2 wt. %.

Measuring the Centrifuge Capacity (C.C.)

The centrifuge capacity (C.C.) is determined by the tea-bag method and expressed as the average of 3 measurements: 660 mg of super-absorbent polymer (SAP) is sealed into a tea bag and immersed in a 0.9% aqueous NaCl solution for 20 minutes. The tea bag is then centrifuged for 5 minutes at 1400 r.p.m. and weighed. An empty tea bag is run alongside it to determine the blank value.

Centrifuge capacity=(end weight−blank value)−initial weight/initial weight [g/g]

The centrifuge capacity of the product obtained in accordance with Example 1 is 42.1 g/g.

Measuring the Gel Strength

Apparatus used: Stevens L.F.R.A. Texture Analyzer.

Measuring principle: a cylindrical or conical test probe is pressed into the gel specimen with a pre-selected speed and measuring length. The resulting force in g is measured and digitally analysed.

Carrying out the measurements: 1 g of the sample to be investigated is swollen in 170 ml of de-ionised water for 2 hours. The gel is then transferred into a 150-ml beaker. After temperature equalisation of the sample at 20° C., the measuring equipment is set at a speed of 1 mm/sec and a penetration path of 10 mm, and to the "normal" test program. The cylindrical test probe designated TA3 with a 1-inch diameter is used as the test probe. At least two measurements are carried out with each sample.

The gel strength of the product obtained in accordance with Example 1 is 106 g.

Examples 2 to 12

The hydrolysis conditions of the samples produced in accordance with Examples 2 to 12 are shown in Table 1.

The properties of the super-absorbent polymers obtained in these hydrolysis tests, having particle size distributions in the range of 100 to 850 μm, may be taken from Table 2.

TABLE 1

| | PAN emulsion | | | | | | Hydrolysis conditions | | | | | | |
|---|---|---|---|---|---|---|---|---|---|---|---|---|---|
| Example | DVB[1] [wt. %] | P.S.[2] [nm] | S.C.[3] [wt. %] | Comonomer | PAN [mol] | alcohol | [C$_o$PAN] wt. % | molar ratio PAN:NaOH | weight ratio H$_2$O:alcohol | temperature [° C.] | residence time | Degree of hydrolysis [wt. %] | Yield [g] |
| 2 | 0.75 | 120 | 23.0 | — | 1.5 | ethanol | 11.6 | 1:0.7 | 1:0.77 | 78.5 | 3.0 | 59.0 | 128.0 |
| 3 | 0.75 | 120 | 23.0 | — | 1.5 | ethanol | 9.0 | 1:1 | 1:1.2 | 78.5 | 5.0 | 66.0 | 132.0 |
| 4 | 0.75 | 73 | 29.0 | — | 1.5 | ethanol | 12.0 | 1:0.7 | 1:1.2 | 78.5 | 3.0 | 58.0 | 130.0 |

TABLE 1-continued

| | PAN emulsion | | | | | | Hydrolysis conditions | | | | | | |
|---|---|---|---|---|---|---|---|---|---|---|---|---|---|
| Example | DVB[1] [wt. %] | P.S.[2] [nm] | S.C.[3] [wt. %] | Comonomer | PAN [mol] | alcohol | $[C_oPAN]$ wt. % | molar ratio PAN:NaOH | weight ratio $H_2O$:alcohol | temperature [° C.] | residence time | Degree of hydrolysis [wt. %] | Yield [g] |
| 5 | 0.75 | 73 | 29.0 | — | 1.3 | ethanol | 10.0 | 1:0.7 | 1:1.75 | 78.5 | 3.0 | 58.6 | 123.0 |
| 6 | 0.75 | 120 | 23.0 | — | 1.5 | methanol | 10.9 | 1:0.7 | 1:0.91 | 71.5 | 6.0 | 55.0 | 123.0 |
| 7 | 0.75 | 72 | 28.9 | MA[d] (7.5%) | 1.3 | methanol | 8.0 | 1:1.5 | 1:1.5 | 71.5 | 4.0 | 50.0 | 102.0 |
| 8 | 1.5 | 70 | 38.3 | MA (10.0%) | 1.4 | methanol | 12.0 | 1:0.7 | 1:2.04 | 71.5 | 6.0 | 58.0 | 114.0 |
| 9 | 0.75 | 120 | 23.0 | — | 7.0 | ethanol | 11.0 | 1:0.5 | 1:0.98 | 100.0 | 2.0 | ca. 50 | 595.0 |
| 10 | — | 150 | 20.9 | — | 3.3 | ethanol | 10.0 | 1:1 | 1:0.83 | 74.5 | 4.0 | 56.0 | 283.0 |
| 11 | — | 150 | 20.9 | — | 3.0 | ethanol | 9.0 | 1:1.25 | 1:0.98 | 74.5 | 5.0 | 63.0 | 254.4 |

[1]DVB: divinylbenzene;
[2]P.S.: particle size;
[3]S.C.: solids content;
[4]MA: methyl acrylate

TABLE 2

| | Average particle diameter [μm] | | Thermal treatment (15 min.) [° C.] | Free degree of swelling [g/g] | | pH value in 0.9% NaCl solution | WSP[1] [wt. %] | C.C.[2] [g/g] | Gel strength [g] |
|---|---|---|---|---|---|---|---|---|---|
| Example | <100 μm | 100–850 μm | | in water | in 0.9% NaCl solution | | | | |
| 2 | 12.0% | 88.0% | 200 | 630 | 57.8 | 6.2 | 8.0 | 45.2 | 96 |
| 3 | 10.1% | 89.9% | 200 | 475 | 50.1 | 6.0 | 7.5 | 38.2 | 102 |
| 4 | 11.0% | 89.0% | 170 | 560 | 59.1 | 5.9 | 8.5 | 47.4 | 82 |
| 5 | 13.5% | 86.5% | 170 | 480 | 53.0 | 6.2 | 7.9 | 39.8 | — |
| 6 | 15.0% | 85.0% | 200 | 609 | 61.0 | 5.9 | 7.5 | 47.0 | — |
| 7 | 17.0% | 83.0% | 200 | 245 | 38.2 | 6.1 | 7.3 | 28.3 | 104 |
| 8 | 30.0% | 70.0% | 165 | 140 | 32.0 | 6.2 | 4.5 | 22.0 | — |
| 9 | 15.0% | 85.0% | 170 | 328 | 42.4 | 5.3 | 6.3 | 33.0 | — |
| 10 | 8.8% | 91.2% | 200 | 480 | 55.0 | 6.3 | 11.0 | 43.0 | — |
| 11 | 10.9% | 89.1% | 220 | 500 | 56.0 | 6.2 | 10.5 | 43.5 | — |

[1]WSP: water-soluble portion;
[2]C.C.: centrifuge capacity

Examples 2 and 3

A PAN emulsion crosslinked with 0.75 wt. % divinylbenzene (DVB), having an average particle diameter of 120 nm and a solids content of 23.0 wt. %, was used as the starting product for the hydrolysis reaction. The hydrolysis was carried out in a water/ethanol mixture according to the method described in Example 1 with an increasing molar ratio of NaOH to PAN and an increasing weight ratio of ethanol to water.

Examples 4 and 5

For these examples a PAN emulsion crosslinked with 0.75 wt. % DVB, having an average particle diameter of 73 nm and a solids content of 29.0 wt. %, was used as the starting product for the hydrolysis. The hydrolysis was carried out in a water/ethanol mixture in accordance with the method given in Example 1. The molar ratio of PAN to NaOH was also 1:0.7 while the water:alcohol weight ratios were varied.

Examples 6 to 8

The hydrolysis reactions were carried out in a water/methanol mixture in the same way as the experiment described in Example 1. Cross-linked PAN emulsions both as a homopolymer (cf. Example 6) and as copolymers with methyl acrylate (Examples 7 and 8) as comonomer were used as starting products.

Example 9

1613 g (7.0 mol) of a PAN emulsion crosslinked with 0.75 wt. % DVB, having an average particle diameter of 120 nm and a solids content of 23.0 wt. %, and 450 g of ethanol are placed in a 6-1 autoclave with stirring. After brief evacuation of the autoclave (approx. 10 mbar) the contents of the reactor are warmed to 50° C. A mixture of 1000 g of ethanol and 311 g (3.5 mol) of a 45 wt. % aqueous NaOH solution is then metered in under vacuum over a 45-minute period.

At the beginning of the reaction the reaction mixture has the following composition: 11.0 wt. % polyacrylonitrile and 4.15 wt. % NaOH, the molar ratio of polyacrylonitrile to NaOH being 1:0.5 and the weight ratio of water to ethanol 1:0.98.

The contents of the reactor are heated to 100° C. and kept at this temperature for 2 hours. After cooling to 20° C. the reactor is depressurised and the ammonia released is absorbed by passing into 1500 ml of a 20% sulphuric acid solution. 790 g of ethanol is then metered into the reactor over a 30 to 40-minute period with stirring. The powdery sediment precipitated during the reaction is discharged through the bottom valve as a suspension. The suspension is neutralised in 2.5 l of a water/ethanol mixture (water:ethanol weight ratio=1:3) with 260 ml of a 5-molar formic acid solution, with stirring. After filtering and washing with 3 l of ethanol and subsequent drying in vacuo at 65° C., approx. 595 g of a powder is obtained, which is graded by sieving without grinding.

The particle size distribution and the properties of this super-absorbent polymer are given in Table 2.

Examples 10 and 11

In Examples 10 and 11 the hydrolysis was carried out in the same way as stated in Example 1. An un-crosslinked emulsion with an [η] value of 7.8 dl/g, an average particle diameter of 150 nm and a solids content of 20.9 wt. % was used as the starting product for the hydrolysis.

What is claimed is:

1. A process for producing pre-formed, spherical, super-absorbent polymers, wherein fine-particle, aqueous emulsions of acrylonitrile homopolymers or copolymers are partially hydrolysed by reaction with alkali metal hydroxide in a water/alcohol mixture, and powders precipitated during the course of the reaction are separated off, dried and optionally heated.

2. A process according to claim 1, wherein the alcohol in the water/alcohol mixture is an aliphatic monohydric alcohol.

3. A process according to claim 2, wherein the alcohol is methanol, ethanol, n-propanol, i-proponal, n-butanol or i-butanol.

4. A process according to claim 1, wherein the weight ratio of water to alcohol is 10:1 to 1:10.

* * * * *

UNITED STATES PATENT AND TRADEMARK OFFICE

CERTIFICATE OF CORRECTION

PATENT NO.: 6,156,848
DATED: December 5, 2000
INVENTOR(S): Günter SACKMANN, Sergej SCHAPOWALOW, Siegfried KORTE, and Rolf-Volker MEYER.

It is certified that error appear in the above-identified patent and that said Letters Patent is hereby corrected as shown below:

<u>In the Claims</u>

Column 8, line 5 (Claim 1), "hydrolysed" should be -- hydrolyzed --.

Column 8, line 6 (Claim 1), after "powders", insert -- of said homopolymers or copolymers --.

Signed and Sealed this

Twenty-fourth Day of April, 2001

NICHOLAS P. GODICI

*Attest:*

*Attesting Officer*   Acting Director of the United States Patent and Trademark Office